United States Patent [19]

Langlois

[11] Patent Number: 4,459,242

[45] Date of Patent: Jul. 10, 1984

[54] METHOD OF PREPARING ALKALINE DIFLUOROMETHANE SULFONATES

[75] Inventor: Bernard Langlois, Lyons, France

[73] Assignee: Rhone-Poulenc Industries, Paris, France

[21] Appl. No.: 422,394

[22] Filed: Sep. 24, 1982

Related U.S. Application Data

[63] Continuation of Ser. No. 202,242, Oct. 30, 1980, abandoned.

[30] Foreign Application Priority Data

Nov. 13, 1979 [FR] France .............................. 79 27889

[51] Int. Cl.³ .......................................... C07C 143/02
[52] U.S. Cl. ................................................. 260/513 B
[58] Field of Search ..................................... 260/513 B

[56] References Cited

PUBLICATIONS

Ehret, "Smith's College Chem.", 6th Ed., (1946), p. 319.
Cotton, "Advanced Inorg. Chem.", 2nd Ed., (1966), p. 546.
Gilbert, "Sulf. and Related Reactions", (1965). pp. 139, 140.
Farrar, "Arylamides of Halogenated Methane and Ethane Sulf. Acids", J. Chem Soc., pp. 3058–3062, (1960).

Primary Examiner—Alan Siegel
Attorney, Agent, or Firm—Herbert F. Schwartz; James F. Haley, Jr.; Eugene S. Indyk

[57] ABSTRACT

A method of preparing alkaline difluoromethane sulfonates by reacting an alkali-metal sulfite of the formula $M_2SO_3$, in which M represents an alkali-metal of column 1 of the Periodic Table of the Elements, with at least an equimolecular quantity of chlorodifluoromethane in aqueous medium, in an autoclave under autogenous pressure, characterized by the fact that the reaction is carried out in the presence of at least one strong alkali-metal base of the formula M'OH, in which M' represents an alkali-metal of column 1 of the Periodic Table of the Elements.

15 Claims, No Drawings

METHOD OF PREPARING ALKALINE DIFLUOROMETHANE SULFONATES

This is a continuation, of application Ser. No. 202,242, filed Oct. 30, 1980 now abandoned.

BACKGROUND OF THE INVENTION

The present invention relates to a method of preparing alkaline difluoromethane sulfonates. More particularly, it concerns the preparation of alkaline difluoromethane sulfonates from chlorodifluoromethane.

In the prior art [J. Chem. Soc., pp. 3058–3062 (1960)], a method is disclosed for preparing sodium difluoromethane sulfonate by reacting chlorodifluoromethane with sodium sulfite in aqueous solution at 120° C. in an autoclave. When operating for 20 hours under an autogenous pressure of 16 bars, the yield indicated in the said publication is 23 percent. In a test carried out by the present applicant, under the same conditions, there was obtained a conversion of only 4.4 percent of the chlorodifluoromethane, with a sodium difluoromethane sulfonate selectivity of 10 percent, which is equivalent to a total yield of only 0.4 percent.

The present applicant has now discovered a method which alleviates the drawbacks of said prior art. The method of the present invention makes it possible to obtain conversion rates of the chlorodifluoromethane and selectivities for alkaline difluoromethane sulfonate which provide a process worthy of interest on an industrial scale. These are important objects of the present invention.

Another object of the present invention is, therefore, to provide an improved method of preparing alkaline difluoromethane sulfonates.

Other objects will be apparent to those skilled in the art from the present description.

GENERAL DESCRIPTION OF THE INVENTION

By the present invention, alkaline difluoromethane sulfonates are prepared by the method of reacting an alkali-metal sulfite of the formula $M_2SO_3$, in which M represents an alkali-metal of column 1 of the Periodic Table of the Elements, with at least an equimolecular amount of chlorodifluoromethane in aqueous medium in an autoclave under autogenous pressure, characterized by the fact that the reaction is carried out in the presence of at least one strong alkali-metal base of the formula M'OH, in which M' represents an alkali-metal of column 1 of the Periodic Table of the Elements.

In accordance with a preferred embodiment of the method of the invention, the strong alkaline base is of a metal which corresponds to the metal of the alkali-metal sulfite. This corresponds to the case in which M and M' represent the same alkali-metal.

The process of the invention is more particularly adapted to the preparation of sodium difluoromethane sulfonate and potassium difluoromethane sulfonate since these are the two compounds which are of the greatest importance industrially.

The overall chemical reaction which takes place in the process of the invention can be written as follows:

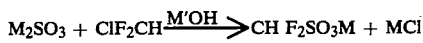

in which M and M' have the meaning given above.

In accordance with one preferred embodiment of the invention, the alkali-metal base, M'OH, is used in such an amount that the molar ratio of the alkali-metal base, M'OH, to the alkaline sulfite, $M_2SO_3$, is between about 0.1 and about 1 to 1. Even more preferably, this ratio is equal to about 0.5 to 1.

It is preferred to operate at a temperature between about 100° C. and about 200° C. Even more preferably, a temperature of about 150° C. is employed. For this temperature range, the autogenous pressure which is generated in the autoclave is between about 10 and about 60 bars.

In accordance with one particular embodiment of the invention, the reaction is carried out in the additional presence of at least one phase transfer agent, preferably selected from among the group consisting of quaternary ammonium and quaternary phosphonium salts. This addition, which is not essential, makes it possible to increase the selectivity for alkaline difluoromethane sulfonate.

The quaternary ammonium and phosphonium salts which can optionally be used in the process of the invention have one of the following general formulas:

and

in which $R_1$, $R_2$, $R_3$, and $R_4$, which are identical or different, each represent a group selected from the class consisting of alkyl, aralkyl, and aryl radicals, optionally substituted, having from about 1 to 24 carbon atoms, and X represents a halogen atom or $HSO_4^-$.

It is preferred to use quaternary ammonium or phosphonium salts in which $R_1$, $R_2$, $R_3$, and $R_4$, whether identical or different, each represent a radical selected from among the class consisting of alkyl radicals having from about 1 to 12 carbon atoms, phenyl radicals and benzyl radicals and in which X represents chlorine or bromine.

The following may be cited as examples of such phase transfer compounds:

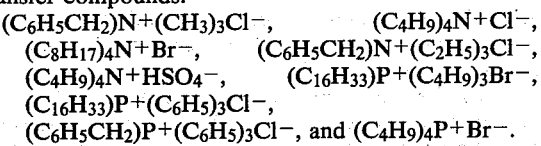

The quaternary ammonium or phosphonium salts are used in such amounts that the molar ratio of the quaternary ammonium or phosphonium salt to the alkaline sulfite is between about 0.02 and about 0.1 to 1. Preferably, this ratio is equal to about 0.05 to 1.

For the method of the invention to proceed optimally, the reaction is carried out in the presence of an amount of water greater than or equal to about 200 ml. per mol of alkali-metal sulfite used. 300 to 700 ml. of water per mol of alkali-metal sulfite introduced into the reaction system are preferably employed.

The alkaline difluoromethane sulfonates, and in particular, sodium difluoromethane sulfonate, are useful, for instance, for the preparation of difluoromethane sulfonyl chloride, which is an important synthesis intermediate, in particular, for the preparation of compounds of pharmaceutical or phytosanitary activity.

SPECIFIC DESCRIPTION OF THE INVENTION

In order to disclose more clearly the nature of the present invention, the following examples illustrating the invention are given. It should be understood, however, that this is done solely by way of example and is intended neither to delineate the scope of the invention nor limit the ambit of the appended claims. In the examples which follow, and throughout the specification, the quantities of material are expressed in terms of parts by weight, unless otherwise specified.

EXAMPLE 1

A mixture of 53.1 g. (0.6 mol) of chlorodifluoromethane, 37.8 g. (0.3 mol) of anhydrous sodium sulfite, 12.0 g. (0.3 mol) of sodium hydroxide (in pellets), and 100 ml. of water was heated in an autoclave for 20 hours at 120° C., under an autogenous pressure of 16 bars. After cooling, degasification of the unreacted chlorodifluoromethane, and opening of the autoclave, the reaction medium was evaporated to dryness. The solid residue obtained was extracted with acetone. 38 g. of acetone-insoluble solid product were recovered and evaporation to dryness of the acetone solution gave 3.7 g. of solid product.

The acetone-insoluble product consisted of unreacted sodium sulfite, sodium chloride (0.117 mol), sodium fluoride (0.091 mol), and a small amount of unextracted sodium difluoromethane sulfonate (0.009 mol). The acetone-soluble product consisted of practically pure sodium difluoromethane sulfonate (0.024 mol), slightly contaminated by sodium fluoride (0.0004 mol).

The ratio between the number of reacted mols of chlorodifluoromethane, $CHF_2Cl$, (indicated by the quantity of $Cl^-$), and the number of convertible mols of $CHF_2Cl$ was 39 percent. The sodium difluoromethane sulfonate selectivity (number of mols of $CHF_2SO_3Na$ formed as compared with the number of mols of $CHF_2Cl$ reacted) was 28 percent. The yield of sodium difluoromethane sulfonate, therefore, amounted to 11 percent.

EXAMPLE 2

A mixture of 40.7 g. (0.47 mol) of chlorodifluoromethane, 18.9 g. (0.15 mol) of anhydrous sodium sulfite, 6.0 g. (0.15 mol) of caustic soda, and 50 ml. of water was heated in an autoclave for 20 hours at 150° C., under an autogenous pressure of 43 bars.

Using the same procedure of treatment of the reaction mixture as in Example 1, 25.1 g. of acetone-insoluble solid product and 5.3 g. of acetone-soluble product were recovered.

The acetone-insoluble portion consisted of unreacted sodium sulfite, sodium chloride (0.156 mol), sodium fluoride (0.127 mol), and unextracted sodium difluoromethane sulfonate (0.011 mol).

The acetone-soluble portion consisted of pure sodium difluoromethane sulfonate (0.035 mol). It was noted that a stoichiometric amount of chlorodifluoromethane had reacted and that the yields of sodium difluoromethane sulfonate was 29 percent.

EXAMPLE 3

A mixture of 156.0 g. (1.8 mol) of chlorodifluoromethane, 151.2 g. (1.2 mol) of anhydrous sodium sulfite, 24 g. (0.6 mol) of sodium hydroxide, and 500 ml. of water was treated under the same conditions as those of Example 2, above, and the products isolated in the same manner. In this way, there were recovered 176 g. of acetone-insoluble solids and 94 g. of acetone-soluble solids. The acetone-insoluble product consisted of unreacted sodium sulfite, sodium chloride (1.122 mol), and sodium fluoride (0.867 mol).

The acetone-soluble product consisted of sodium difluoromethane sulfonate pure in $NMR^{19}F$ (0.612 mol).

The ratio between the number of reacted mols of $CHF_2Cl$ and the number of convertible mols of $CHF_2Cl$ was 93.5 percent, and the selectivity for sodium difluoromethane sulfonate was 54.5 percent, which brings the yield of $CHF_2SO_3Na$ to 51 percent.

COMPARATIVE EXAMPLE

A mixture of 0.45 mol of $CHF_2Cl$, 0.3 mol of sodium sulfite, and 125 ml. of water was treated as in Example 3, above, and the products isolated in the same manner.

The ratio between the number of reacted mols of $CHF_2Cl$ and the number of convertible mols of $CHF_2Cl$ was 70 percent, and the selectivity for sodium difluoromethane sulfonate was 24 percent, which brought the yield of $CHF_2SO_3Na$ to 17 percent.

EXAMPLE 4

A mixture of 79.0 g. (0.91 mol) of chlorodifluoromethane, 37.8 g. (0.30 mol) of anhydrous sodium sulfite, 6.0 g. (0.15 mol) of sodium hydroxide, 8.2 g. (0.015 mol) of tetra-n-octylammonium bromide, and 100 ml. of water was treated under the same conditions as in Example 3, above, and the products isolated in the same manner.

There were obtained 43.9 g. of acetone-insoluble solids and 14.5 g. of acetone-soluble solids. The acetone-insoluble portion consisted of unreacted sodium sulfite, sodium chloride (0.208 mol), sodium fluoride (0.126 mol), and unextracted sodium difluoromethane sulfonate (0.027 mol).

The acetone-soluble portion consisted of sodium difluoromethane sulfonate (0.088 mol) and ammonium difluoromethane sulfonate (0.001 mol) which could be distinguished from sodium difluoromethane sulfonate in $NMR^{19}F$.

The ratio between the number of reacted mols of $CHF_2Cl$ and the number of convertible mols of $CHF_2Cl$ was 69 percent, and the selectivity in difluoromethane sulfonate was 56 percent, which brings the yield of $CHF_2SO_3^-$ to 39 percent.

EXAMPLE 5

A mixture of 0.9 mol of chlorodifluoromethane, 0.3 mol of potassium sulfite, 0.3 mol of potassium hydroxide, and 100 ml. of water was treated under the same conditions as in Example 2, above, and the products isolated in the same manner. In this way, potassium difluoromethane sulfonate was obtained in a yield of 41 percent with respect to the potassium sulfite employed.

As will be apparent to those skilled in the art, other quaternary ammonium and phosphonium compounds, such as those disclosed herein, may be substituted for the tetra-n-octylammonium bromide, employed in Example 4, above.

As used herein to refer to the metals, M and M', column 1 of the Periodic Table of the Elements, as approved by the American Chemical Society, is intended. These metals include the well-known "alkali-metals," of which sodium, potassium, and lithium are the most well known. Because of its greater availability, sodium is preferred.

The terms and expressions which have been employed are used as terms of description and not of limitation, and there is no intention in the use of such terms and expressions of excluding any equivalents of the features shown and described or portions thereof, but it is recognized that various modifications are possible within the scope of the invention claimed.

What is claimed is:

1. A method of preparing alkaline difluoromethane sulfonates which comprises reacting an alkali-metal sulfite of the formula $M_2SO_3$, in which M represents an alkali-metal of column 1 of the Periodic Table of the Elements, with an at least equimolecular amount of chlorodifluoromethane, in an aqueous medium, in an autoclave under autogenous pressure, whereby the said reaction is carried out in the presence of at least one strong alkali-metal base of the formula M'OH in which M' represents an alkali-metal of column 1 of the Periodic Table of the Elements.

2. A method according to claim 1, wherein M' and M represent the same alkali-metal.

3. A method according to claim 1, wherein M' and M represent an alkali-metal selected from the class consisting of sodium and potassium.

4. A method according to claim 1, wherein the said alkali-metal base is used in such amount that the molar ratio of the alkali-metal base to the alkali-metal sulfite is between about 0.1 and about 1 to 1.

5. A method according to claim 4, wherein the molar ratio of the alkali-metal base to the alkali-metal sulfite is equal to about 0.5 to 1.

6. A method according to claim 1, wherein the reaction is carried out at a temperature of between about 100° C. and about 200° C.

7. A method according to claim 6, wherein the reaction is carried out at a temperature of about 150° C.

8. A method according to any one of claims 1 to 7, wherein the reaction is carried out in the presence of at least one phase transfer agent.

9. A method according to claim 8, wherein the said phase transfer agent is selected from the group consisting of quaternary ammonium salts and quaternary phosphonium salts.

10. A method according to claim 9, wherein the said quaternary ammonium salts and the said quaternary phosphonium salts have one of the following formulas:

$$R_1R_2R_3R_4N^+X^-$$

and $$R_1R_2R_3R_4P^+X^-$$

in which $R_1$, $R_2$, $R_3$, and $R_4$, each represent a group selected from the class consisting of alkyl, aralkyl, and aryl radicals, having from about 1 to 24 carbon atoms, and X represents a member selected from the class consisting of a halogen atom and $HSO_4^-$.

11. A method according to claim 10, wherein the said quaternary ammonium and the said phosphonium salt is selected from the group consisting of:
$(C_6H_5CH_2)N^+(CH_3)_3Cl^-$, $(C_4H_9)_4N^+Cl^-$, $(C_8H_{17})_4N^+Br^-$, $(C_6H_5CH_2)N^+(C_2H_5)_3Cl^-$, $(C_4H_9)_4N^+HSO_4^-$, $(C_{16}H_{33})P^+(C_4H_9)_3Br^-$, $(C_{16}H_{33})P^+(C_6H_5)_3Cl^-$, $(C_6H_5CH_2)P^+(C_6H_5)_3Cl^-$, and $(C_4H_9)_4P^+Br^-$.

12. A method according to claim 9, wherein the molar ratio of the quaternary ammonium salt to the alkali-metal sulfite is between about 0.02 and about 0.1 to 1.

13. A method according to claim 12, wherein the molar ratio of the quaternary ammonium salt to the alkali-metal sulfite is equal to about 0.05 to 1.

14. A method according to claim 1, wherein the reaction is carried out in the presence of at least 200 ml. of water per mol of alkali-metal sulfite used.

15. A method according to claim 14, wherein the reaction is carried out in the presence of about 300 ml. to about 700 ml. of water per mol of alkali-metal sulfite used.

* * * * *